US005595737A

United States Patent [19]
Tedder et al.

[11] Patent Number: 5,595,737
[45] Date of Patent: Jan. 21, 1997

[54] METHODS FOR USING MONOCLONAL ANTIBODIES SPECIFIC FOR CELL-SURFACE BOUND LAM-1

[75] Inventors: Thomas F. Tedder, South Natick; Boris Schleiffenbaum, Brookline, both of Mass.; Olivier Spertini, Assens, Switzerland

[73] Assignee: Dana-Farber Cancer Institute, Inc., Boston, Mass.

[21] Appl. No.: 477,394

[22] Filed: Jun. 7, 1995

Related U.S. Application Data

[62] Division of Ser. No. 334,191, Nov. 4, 1994, which is a division of Ser. No. 862,483, Apr. 2, 1992, Pat. No. 5,389,520, which is a continuation-in-part of Ser. No. 730,503, Jul. 8, 1991, abandoned, which is a continuation of Ser. No. 313,109, Feb. 21, 1989, abandoned, and a continuation-in-part of Ser. No. 700,773, May 15, 1991, abandoned, Ser. No. 737,092, Jul. 29, 1991, abandoned, and Ser. No. 770,608, Oct. 3, 1991, abandoned.

[51] Int. Cl.$^6$ .................... A61K 39/395; C07K 16/28; C12N 5/20
[52] U.S. Cl. .................... 424/130.1; 530/388.22; 530/388.73; 530/388.75; 435/240.27
[58] Field of Search .................... 530/387.9, 388.2, 530/388.22, 388.73, 389.7, 389.6, 388.75; 435/70.21, 172.2, 240.27, 7.24; 424/139.1, 144.1, 153.1, 173.1

[56] References Cited

U.S. PATENT DOCUMENTS

| | | |
|---|---|---|
| 4,840,793 | 6/1989 | Todd, III et al. . |
| 4,959,302 | 9/1990 | Cornaby et al. . |
| 5,002,873 | 3/1991 | St. John et al. . |
| 5,098,833 | 3/1992 | Lasky et al. . |

OTHER PUBLICATIONS

Harris & Emery, TIBTECH vol. N:44–46 1993.
Springer, "Adhesion receptors of the immune system," Nature 346:425–434 (1990).
Kishimoto et al., "Identification of a human peripheral lymph node homing receptor: A rapidly down–regulated adhesion molecule," Proc. Natl. Acad. Sci. USA 87:2244–2248 (1989).
Ley et al., "Lectin–Like Cell Adhesion Molecule1 Mediates Leukocyte Rolling in Mesenteric Venules in Vivo," Blood 77:2553–2555 (1991).
Spertini et al., "Leukocyte Adhesion Molecule (LAM-1, L–Selectin) Interacts with an Inducible Endothelial Cell Ligand to Support Leukocyte Adhesion," J. Immunol. 147:2565–2573 (1991).
Bowen et al., "Characterization of a Human Homologue of the Murine Peripheral Lymph Node Homing Receptor," J. Cell Biol. 109:421–427 (1989).
Siegelman et al., "Human homologue of mouse lymph node homing receptor: Evolutionary conservation at tandem cell interaction domains," Proc. Natl. Acad. Sci. USA 86: 5562–5566 (1989).

Tedder et al., "Isolation and Chromosomal Localization of cDNAs Encoding a Novel Human Lymphocyte Cell Surface Molecule, LAM–1," J. Exp. Med. 170: 123–133 (1989).
Gallatin et al., "A cell–surface molecule involved in organ–specific homing of lymphcytes," Nature 304: 30–34 (1983).
Lasky et al., "Cloning of a Lymphocyte Homing Receptor Reveals a Lectin Domain," Cell 56: 1045–1055 (1989).
Siegelman et al., "Mouse Lymph Node Homing Receptor cDNA Clone Encodes a Glycoprotein Revealing Tandem Interactions Domains," Science 243: 1165–1172 (1989).
Bevilacqua et al., "Identification of an inducible endothelial–leukocyte adhesion molecule," Proc. Natl. Acad. Sci. USA 84:9238–9243 (1987).
Bevilacqua et al., "Endothelial Leukocyte Adhesion Molecule 1: An Inducible Receptor for Neutrophils Related to Complement Regulatory Proteins and Lectins," Science 243: 1160–1164 (1989).
Luscinskas et al., "Endothelial–leukocyte adhesion molecule–1–dependent and leukocyte (CD11/CD18)–dependent mechanisms contribute to polymorphonuclear leukocyte adhesion to cytokine–activated human vascular endothelium," J. Immunol. 142: 2257–2263 (1989).
Luscinskas et al., "Cytokine–activated human endothelial monolayers support enhanced neutrophil transmigration via a mechanism involving both endothelial–leukocyte adhesion molecule–1 and intercellular adhesion molecule–1," J. Immunol. 146: 1617–1625 (1991).
Geng et al., "Raped neutrophil adhesion to activated endothelium mediated by GMP–140," Nature 323: 757–760 (1990).
Johnston et al., "Cloning of GMP–140, a Granule Membrane Protein of Platelets and Endothelium: Sequence Similarity to Proteins Involved in Cell Adhesion and Inflammation," Cell 56: 1033–1044 (1989).
Larsen et al., "PADGEM Protein: A receptor that mediates the Interaction of activated platelets with neutrophils and monocytes," Cell 59: 305–312 (1989).
Larsen et al., "PADGEM–Dependent adhesion of platelets to monocytes and neutrophils is mediated by a lineage–specific carbohydrate, LNF III(CD 15)," Cell 63: 467–474 (1990).

(List continued on next page.)

Primary Examiner—Paula K. Hutzell
Assistant Examiner—Nancy A. Johnson
Attorney, Agent, or Firm—Fish & Neave; James F. Haley, Jr.; Jane T. Gunnison

[57] ABSTRACT

A shed form of leukocyte adhesion molecule-1 (LAM-1, L-selectin) is present in high levels in human plasma. Quantitative methods of detecting shed LAM-1 (sLAM-1) by Western blot and ELISA analysis are disclosed. Also disclosed are methods for the specific detection of cell-surface bound LAM-1 in the presence of shed LAM-1 and for immunotherapy using monoclonal antibodies reactive with cell-surface bound LAM-1 but not reactive with shed LAM-1.

2 Claims, No Drawings

OTHER PUBLICATIONS

Collins et al., "Structure and Chromosomal Location of the Gene for Endothelial–Leukocyte Adhesion Molecule 1," *J. Biol. Chem.* 266: 2466–2473 (1991).

Johnston et al., "Structure of the Human Gene Encoding Granule Membrane Protein–140, a Member of the Selectin Family of Adhesion Receptors for Leukocytes," *J. Biol. Chem.* 265: 21381–21385 (1990).

Ord et al., "Structure of the Gene Encoding the Human Leukocyte Adhesion Molecule–1 (TQ1, Leu–8) of Lymphocytes and Neutrophils," *J. Biol. Chem.* 265: 7760–7767 (1990).

Watson et al., "Genomic Organization of the Selectin Family of Leukocyte Adhesion Molecules on Human and Mouse Chromosome 1," *J. Exp. Med.* 172: 263–272 (1990).

Griffin et al., "Granulocyte–Macrophage Colony–Stimulating Factor and Other Cytokines Regulate Surface Expression of the Leukocyte Adhesion Molecule–1 on Human Neutrophils, Monocytes, and their Precursors," *J. Immunol.* 145: 576–584 (1990).

Tedder et al., "Expression of the Human Leukocyte Adhesion Molecule, LAM–1: Identity with the TQ1 and Leu–8 Differentiation Antigens," *J. Immunol.* 144: 532–540 (1990).

Tedder et al., "Human antigen–specific memory T cells express the homing receptor (LAM–1) necessary for lymphocyte recirculation," *Eur. J. Immunol.* 20: 1351–1355 (1990).

Imai et al., "Identification of a carbohydrate–based endothelial ligand for a lymphocyte homing receptor," *J. Cell Biol.* 113: 1213–1221 (1991).

Spertini et al., "Regulation of Leukocyte Adhesion Molecule–1 (TQ1, Leu–8) Expression and Shedding by Normal and Malignant Cells," *Leukemia* 5: 300–308 (1991).

Stamper et al., "Lymphocyte homing into lymph nodes: In vitro demonstration of the selective affinity of recirculating lymphocytes for high–endothelial venules," *J. Exp. Med.* 144: 828–833 (1976).

Hallmann et al., "The peripheral lymph node homing receptor, LECAM–1, is involved in CD18–independent adhesion of human neutrophils to endothelium," *Biochem. Biophys. Res. Comm.* 174: 236–243 (1991).

Jutila et al., "Function and Regulation of the Neutrophil MEL–14 Antigen in vivo: Comparison with LFA–1 and MAC–1," *J. Immunol.* 143:3318–3324 (1989).

Lewinsohn et al., "Leukocyte–endothelial cell recognition: Evidence of a common molecular mechanism shared by neutrophils, lymphocytes, and other leukocytes," *J. Immunol.* 138: 4313–4321 (1987).

Smith et al., "Chemotactic factors regulate lectin adhesion molecule 1 (LECAM–1)–dependent neutrophil adhesion to cytokine–stimulated endothelial cells in vitro," *J. Clin. Invest.* 87: 609–618 (1991).

Watson et al., "Neutrophil influx into an inflammatory site inhibited by a soluble homing receptor–IgG chimaera," *Nature* 349: 164–167 (1991).

Kansas et al., "Molecular Mapping of Functional Domains of The Leukocyte Receptor for Endothelium, LAM–1," *J. Cell Biol.* 114: 351–358(1991).

Stoolman et al., "Homing Receptors on Human and Rodent Lymphocytes–Evidence for a Conserved Carbohydrate–Binding Specificity," *Blood* 70: 1842–1850 (1987).

Yednock et al., "Receptors involved in Lymphocyte Homing: Relationship between a carbohydrate–binding Receptor and the MEL–14 Antigen," *J. Cell Biol.* 104: 725–731 (1987).

Yednock et al., "Phosphomannosyl–derivatized beads detect a receptor involved in lymphocyte homing," *J. Cell Biol.* 104: 713–724 (1987).

Siegelman et al., "The mouse lymph node homing receptor is identical with the lymphocyte cell surface marker Ly–22: Role of the EGF domain in endothelial binding," *Cell* 61: 611–622 (1990).

Spertini et al., "Function and Evolutionary Conservation of Distinct Epitopes on the Leukocyte Adhesion Molecule–1 (TQ1, Leu–8) that Regulate Leukocyte Migration," *J. Immunol.* 147: 942–949 (1991).

Watson et al., "The complement binding–like domains of the murine homing receptor facilitate lectin activity," *J. Cell Biol.* 115: 235–243 (1991).

Jung et al., "Rapid Modulation of Homing Receptors ($gp90^{MEL-14}$) Induced by Activators of Protein Kinase C," *J. Immunol.* 144: 130–136 (1990).

Kishimoto et al., "Neutrophil Mac–1 and MEL–14 adhesion proteins inversely regulated by chemotactic factors," *Science* 245: 1238–1241 (1989).

Chin et al., "Lymphocyte Recognition of Lymph Node High Endothelium. I. Inhibition of an In Vitro Binding by a Component of Thoracic Duct Lymph," *J. Immunol.* 125: 1764–1769 (1980).

Chin et al., "Lymphocyte Recognition of Lymph Node High Endothelium, II. Characterization of an In Vitro Inhibitory Factor Isolated by Antibody Affinity Chromatography," *J. Immunol.* 125: 1770–1774 (1980).

Chin et al., "Lymphocyte Recognition of Lymph Node High Endothelium, V. Isolation of Adhesion Molecules from Lysates of Rat Lymphocytes," *J. Immunol.* 131: 1368–1374 (1983).

Tedder, "Cell–surface Receptor Shedding: A Means of Regulating Function," *Am. J. Respir. Cell Mol. Biol.* 5: 305–307 (1991).

Porteau et al., "Shedding of Tumor Necrosis Factor Receptors by Activated Human Neutrophils," *J. Exp. Med.* 172: 599–607 (1990).

Downing et al., "Ligand and Protein Kinase C Downmodulate the Colony Stimulating Factor 1 Receptor by Independent Mechanisms," *Mol. Cell. Biol.* 9: 2890–2896 (1989).

DiStefano et al., "Identification of a truncated form of the nerve growth factor receptor," *Proc. Natl. Acad. Sci. USA* 85: 270–274 (1988).

Reinherz et al., "Heterogeneity of Human T4[#]Inducer T Cells Defined by a Monoclonal Antibody that Delineates Two Functional Subpopulations," *J. Immunol.* 128: 463–468 (1982).

Wu et al., "Evolutionary Conservation of Tissue–specific Lymphocyte–Endothelial Cell Recognition Mechanisms involved in Lymphocyte Homing," *J. Cell. Biol.* 107: 1845–1850 (1988).

Stoolman, "Adhesion Molecules Controlling Lymphocyte Migration," *Cell* 56: 907–910 (1989).

Osborn, "Leukocyte Adhesion to Endothelium in Inflammation," *Cell* 62: 3–6 (1990).

L. H. Hood et al., "IMMUNOLOGY, Second Edition", The Benjamin/Cummings Publishing Co., Inc., pp. 66–68 (1984).

METHODS FOR USING MONOCLONAL ANTIBODIES SPECIFIC FOR CELL-SURFACE BOUND LAM-1

RELATED APPLICATIONS

This application is a division of application Ser. No. 08/334,191, filed Nov. 4, 1994 entitled: SPECIFIC DETECTION OF CELL SURFACE RECEPTOR LEUKOCYTE ADHESION MOLECULE-1, which is a divisional of application Ser. No. 07/862,483, filed Apr. 2, 1992 (now U.S. Pat. No. 5,389,520, issued Feb. 14, 1995) which is a continuation-in-part of Ser. No. 07/730,503, filed Jul. 8, 1991 (now abandoned), which is a Continuation of Ser. No. 07/313,109, filed Feb. 21, 1989 (now abandoned) and a Continuation-in-Part of Ser. No. 07/700,773, filed May 15, 1991 (now abandoned) and a Continuation-in-part of Ser. No. 07/737,092, filed Jul. 29, 1991 (now abandoned) and a Continuation-in-Part of Ser. No. 07/770,608, filed Oct. 3, 1991, (now abandoned).

FIELD OF THE INVENTION

This invention relates to human leukocyte-associated cell surface proteins, particularly to leukocyte adhesion molecule-1 (LAM-1) and methods for its detection.

Part of the work leading to this invention was made with United States Government funds. Therefore, the U.S. Government has certain rights in this invention.

BACKGROUND OF THE INVENTION

The ability of leukocytes to leave the circulation and to migrate into tissues is a critical feature of the immune response. Normally, the infiltrating leukocytes phagocytize invading organisms or dead or damaged cells. However, in pathologic inflammation, infiltrating leukocytes can cause serious and sometimes deadly damage. Leukocyte-mediated inflammation is implicated in a number of human clinical manifestations, including the adult respiratory distress syndrome, multi-organ failure and reperfusion injury.

Several different receptor adhesion molecules participate in the process of adhesion and transmigration of leukocytes through vascular endothelium at sites of inflammation (Springer, Nature 346:425–434 (1990)). One of the several molecules involved in the initial attachment of leukocytes to endothelium is the leukocyte adhesion molecule-1 (LAM-1, L-selectin) (Kishimoto et al., Proc. Natl. Acad. Sci. USA 87:2244–2248 (1990); Ley et al., Blood 77:2553–2555 (1991); Spertini et al., J. Immunol. 147:2565–2573 (1991)). LAM-1 is a member of the selectin family of adhesion molecules (Bowen et al., J. Cell Biol. 109:421–427 (1989); Siegelman et al., Proc. Natl. Acad. Sci. USA 86:5562–5566 (1989); Tedder et al., J. Exp. Med. 170:123–133 (1989)) that includes, the mouse L-selectin, MEL-14 (Gallatin et al., Nature 304:30–34 (1983); Lasky et al., Cell 56:1045–1055 (1989); Siegelman et al., Science 243:1165–1172 (1989)), Endothelial-Leukocyte Adhesion Molecule-1 (ELAM-1, E-selectin) (Bevilacqua et al., Proc. Natl. Acad. Sci. USA 84:9238–9243 (1987); Bevilacqua et al., Science 243:1160–1164 (1989); Luscinskas et al., J. Immunol. 1422257 (1989); Luscinskas et al., J. Immunol. 146:1617–1625 (1991)), and CD62 (PADGEM, GMP-140, P-selectin) (Geng et al., Nature 343:757–760 (1990); Johnston et al., Cell 56:1033–1044 (1989); Larsen et al., Cell 59:305–312 (1989); Larsen et al., Cell 63:467–474 (1990)). All selectins are derived from evolutionarily related genes (Collins et al., J. Biol. Chem. 266:2466–2478 (1991); Johnston et al., J. Biol. Chem. 34:21381–21385 (1990); Ord et al., J. Biol. Chem. 265:7760–7767 (1990); Watson et al., J. Exp. Med. 172:263–272 (1990)), and are characterized by an $NH_2$-terminal, $Ca^+$-dependent lectin domain, an epidermal growth factor (EGF)-like domain followed by multiple short consensus repeat (SCR) domains, a transmembrane region, and a cytoplasmic tail.

LAM-1 is expressed on the surface of most leukocytes, including lymphocytes, neutrophils, monocytes, eosinophils, hematopoietic progenitor cells and immature thymocytes (Griffin et al., J. Immunol. 145:576–584 (1990); Tedder et al., J. Immunol. 144:532–540 (1990)). LAM-1 is a highly glycosylated protein of 95–105,000 $M_r$ on neutrophils and 74,000 $M_r$ on lymphocytes (Griffin et al., J. Immunol. 145:576–584 (1990); Tedder et al., Eur. J. Immunol. 20:1351–1355 (1990)). Human LAM-1 and mouse MEL-14 mediate the binding of lymphocytes to high endothelial venules (HEV) of peripheral lymph nodes through interactions with a constitutively expressed ligand (Imai et al., J. Cell Biol. 113:1213–1221 (1991); Kishimoto et al., Proc. Natl. Acad. Sci. USA 87:2244–2248 (1990); Spertini et al., Leukemia 5:300–308 (1991); Stamper Jr. et al., J. Exp. Med. 144:828–833 (1976); Tedder et al., J. Immunol. 144:532–540 (1990)), and are also involved in lymphocyte, neutrophil and monocyte attachment at sites of inflammation (Hallmann et al., Biochem. Biophys. Res. Commun. 174:236–243 (1991); Jutila et al., J. Immunol. 143:3318–3324 (1989); Lewinsohn et al., J. Immunol. 138:4313–4321 (1987); Smith et al., J. Clin. Invest. 87:609–618 (1991); Spertini et al., J. Immunol. 147:2565–2573 (1991); Watson et al., Nature 349:164–167 (1991)). In vitro, endothelial cell surface expression of the LAM-1 ligand(s) is induced only after exposure of the endothelial cells to inflammatory cytokines, and the endothelial ligand shares many functional features with the LAM-1 ligand(s) expressed by HEV (Smith et al., J. Clin. Invest. 87:609–618 (1991); Spertini et al., J. Immunol. 147:2565–2573 (1991)). Sulfated carbohydrates and mAb that bind to the lectin domain of LAM-1 inhibit LAM-1-specific adhesion (Imai et al., J. Cell Biol. 113:1213–1221 (1991); Kansas et al., J. Cell Biol. 114:351–358 (1991); Spertini et al., J. Immunol. 147:2565–2573 (1991); Stoolman et al., Blood 70:1842–1850 (1987); Yednock et al., J. Cell Biol. 104:725–731 (1987); Yednock et al., J. Cell. Biol. 104:713–723 (1987)). The lectin domain of LAM-1 seems to act as the ligand binding unit to determine specificity, while the EGF-like and SCR domains appear to regulate the affinity of this interaction (Kansas et al., J. Cell Biol. 114:351–358 (1991); Siegelman et al., Cell 61:611–622 (1990); Spertini et al., J. Immunol. 147:942–949 (1991); Watson et al., J. Cell Biol. 115:235 (1991)).

It has been proposed that the treatment of a patient suffering from pathologic inflammation with an antagonist to adhesion receptor function can result in the reduction of leukocyte migration to a level manageable by the target endothelial cells and the subsequent dramatic recovery of the patient. Local administration of therapeutic agents can block competitively the adhesive interactions between leukocytes and the endothelium adjacent to an inflamed region. Therapeutic agents can also be administered on a systemic level for the treatment of a patient suffering from disseminated inflammation (Harlan and Liu, eds., *Adhesion: Its Role in Inflammatory Disease*, W. H. Freeman (in press)).

A unique feature of the L-selectins is that both human LAM-1 and mouse MEL-14 are shed from the cell surface following cellular activation in vitro (Griffin et al., J. Immunol. 145:576–584 (1990); Jung et al., J. Immunol.

144:3130–3136 (1990); Kishimoto et al., Science 245:1238–1241 (1989); Kishimoto et al., Proc. Natl. Acad. Sci. USA 87:2244–2248 (1990); Spertini et al., Leukemia 5:300–308 (1991)). It has been proposed for the mouse that shedding of MEL-14 from leukocytes might be necessary to enable the leukocytes to transmigrate through endothelium into sites of inflammation in vivo (Jutila et al., J. Immunol. 143:3318–3324 (1989); Kishimoto et al., Science 245:1238–1241 (1989)). This would provide a rapid means for the regulation of leukocyte adhesion and de-adhesion to endothelium. Although the subsequent fate and possible function of the shed LAM-1 (sLAM-1) molecule is not known, the presence of a soluble factor present in rat thoracic duct lymph capable of inhibiting lymphocyte binding to HEV has been demonstrated (Chin et al., J. Immunol. 125:1764–1769 (1980)). Furthermore, this factor was shown to be antigenically related to a structure(s) present on lymphocytes (Chin et al., J. Immunol. 125:1764–1769 (1980); Chin et al., J. Immunol. 125:1770–1774 (1980); Chin et al., J. Immunol. 131:1368–1374 (1983)).

A number of surface molecules present on cells of various lineages are now known to be shed and thereby released into the extracellular milieu (Tedder, Am. J. Respir. Cell Mol. Biol. 5:305–306 (1991)). These include many of the growth factor receptors, the receptors for interleukin-1, interleukin-2 (CD25), transferrin (CD72), insulin, growth hormone, tumor necrosis factor (Porteu et al., J. Exp. Med. 172:599–607 (1990)), colony-stimulation factor-1 (Downing et al., Mol. Cell. Biol. 9:2890–2896 (1989)) and nerve growth factor (DiStefano et al., Proc. Natl. Acad. Sci. USA 85:270–274 (1988)) as well as CD8, and CD14. These proteins are quite diverse in structure and amino acid sequence and have no unifying functional characteristics that are currently appreciated. In most cases, proteases cleave the receptor near the membrane, releasing a nearly intact extracellular domain (DiStefano et al., Proc. Natl. Acad. Sci. USA 85:270–274 (1988); Downing et al., Mol. Cell. Biol. 9:2890–2896 (1989); Kishimoto et al., Science 245:1238–1241 (1989); Spertini et al., Leukemia 5:300–308 (1991)).

No definitive functions for shed receptors have been elucidated, although many of the shed receptors retain ligand-binding activity. Thus, receptor function may be regulated not only by proteolytic cleavage of the receptor from the cell surface, but also by the presence of shed receptor in the extracellular environment.

If the shed form of LAM-1 retains ligand-binding activity, however, one consequence of its presence might be a potential interference with diagnostic or therapeutic administration of antagonists to LAM-1 function. The shed form of the receptor, if present in large amounts, could competitively bind any administered LAM-1 antagonist, thus thwarting the diagnostic effort or the treatment regimen.

SUMMARY OF THE INVENTION

We report here that the shed leukocyte adhesion molecule-1 (sLAM-1) from both lymphocytes and neutrophils was demonstrated to be present in high levels in human plasma. Two assay methods have been used, Western blot analysis and a specially developed, quantitative enzyme-linked immunosorbent assay or ELISA. Semipurified sLAM-1 from plasma inhibited LAM-1-specific attachment of lymphocytes to cytokine-activated endothelium in a dose dependent manner. Total inhibition of LAM-1-dependent lymphocyte attachment was achieved at sLAM-1 concentrations of 8 to 15 µg/ml, while physiological concentrations of sLAM-1 caused a small but consistent inhibition of lymphocyte attachment. sLAM-1 in plasma also inhibited binding of most anti-LAM-1 mAb (2 to 5 µg/ml) to the surface of leukocytes. However, one epitope present within the EGF-like domain of LAM-1 was lost in sLAM-1, suggesting a conformational change in the structure of the receptor after shedding.

The inhibition of LAM-1 dependent lymphocyte attachment by the shed form of the receptor, even at physiological concentrations of sLAM-1, and the inhibition of binding of most anti-LAM-1 mAb could present substantial problems for therapeutic regimens requiring systemic administration of antagonists to LAM-1 function or for diagnostic techniques. The presence of sLAM-1 could require that such agents be administered in excessive doses to be effective. However, our discovery of a difference in epitopes between the EGF-like domains of the LAM-1 molecule and its shed form has permitted the development of diagnostic and therapeutic agents that react with cell surface bound receptor LAM-1 without binding to the shed form of the molecule.

In one aspect the invention generally features monoclonal antibody reactive with LAM-1, and not reactive with shed LAM-1, and a method for isolating the antibody. Preferably, the antibody has the same pattern of reactivity with LAM-1 as monoclonal antibody anti-LAM1-1; most preferably the antibody is anti-LAM1-1 monoclonal antibody. The invention also features methods of using the selective antibody in diagnostic and therapeutic applications.

In another aspect, the invention features a method for quantitating the amount of LAM-1 or fragment thereof in a sample that includes reacting the sample in a binding assay with a binding agent or ligand for LAM-1 or fragment thereof, and comparing the results of the binding assay to a standard curve. Preferably, the fragment of LAM-1 to be detected is shed LAM-1; the sample to be assayed is a biological sample, most preferably the sample is from a patient and the amount of LAM-1 or fragment determined in the binding assay is to be used as a diagnostic variable; the binding assay is either an ELISA or a Western blot; and the binding agent is an anti-LAM-1 antibody.

In another aspect, the invention features a kit for use in quantitating the amount of LAM-1 or fragment thereof in a sample. The kit includes components required for extraction of the sample and components necessary for use in a binding assay, including a binding agent or ligand for LAM-1 or fragments thereof.

Other features and advantages of the invention will be apparent from the following description of the preferred embodiments thereof and from the claims.

DESCRIPTION OF THE PREFERRED EMBODIMENTS

Development of the sLAM-1-ELISA allowed for the first time an easy, efficient and sensitive method for quantification of sLAM-1. The direct demonstration of sLAM-1 in plasma and supernatant fluid from activated neutrophils and lymphocytes confirms that the in vivo and in vitro loss of LAM-1 leukocyte surface expression is due to shedding. The extent of shedding is high; in a population of normal healthy blood donors the mean serum level of sLAM-1 was determined to be 1.6±0.8 µg/ml.

The shed form of LAM-1 was found to be different from the cell surface-bound form in one major way. sLAM-1 did not contain the epitope within the EGF-like domain of LAM-1 identified by the anti-LAM1-1 mAb, while this epitope is readily demonstrated on cell-surface LAM-1 (Kansas et al., J. Cell Biol. 114:351–358 (1991); Spertini et al., J. Immunol. 147:942–949 (1991); Tedder et al., J. Immunol. 144:532–540 (1990)). This was revealed both by ELISA analysis and by a lack of competitive inhibition in immunofluorescence staining of leukocytes. Since the EGF-like domain is retained in sLAM-1, it is possible that alterations in the tertiary structure of LAM-1 occur following shedding that result in a lack of anti-LAM1-1 mAb binding. This loss of reactivity does not appear to be due to technical problems as the LAM-1 epitope was readily demonstrated to be present on a soluble LAM-IgG fusion protein.

Detection and Characterization of sLAM-1 sLAM-1 in serum appears to be derived from both lymphocytes and neutrophils since the analysis of sLAM-1 isolated from neutrophils (95–105,000 $M_r$) and lymphocytes (74,000 $M_r$) produced bands of corresponding $M_r$. The differences in $M_r$ between lymphocyte and neutrophil sLAM-1 most likely result from differences in glycosylation of a single protein species since only a single LAM-1 mRNA species has been identified (Ord et al., J. Biol. Chem. 265:7760–7767 (1990)). Cleavage of LAM-1 to produce sLAM-1 is likely to be proximal to the transmembrane region encoded by exon VIII (Ord et al., supra); cleavage in this region would account for the small difference in $M_r$ between the intact cellular LAM-1 molecule and its shed form (Kishimoto et al., Proc. Natl. Acad. Sci. USA 87:2244–2248 (1990); Lasky et al., Cell. 56:1045–1055 (1989); Spertini et al., Leukemia 5:300–308 (1991)).

The concentration of sLAM-1 was determined by comparison with a reference plasma sample that ranged between 0.85 to 1.9 µg/ml, having been standardized by two independent means. The mean of this range of values of 1.3 µg/ml should represent a conservative estimate of the actual amount of sLAM-1 present in plasma, and was therefore chosen as the basis of all future calculations. Theoretical considerations based on experimental data derived from shedding experiments in K562-LAM-1 transfectants further substantiate the validity of this estimate. Assuming that 30 to 40,000 LAM-1 molecules are present on each K562-LAM cell, and that all molecules (MW 71,000) are shed following PMA stimulation, the concentration of sLAM in plasma can be calculated by comparing the concentration of sLAM-1 (1.7% the concentration of standard plasma) shed from K562 transfectants ($1\times10^7$ cells/ml) to a titration curve of standard plasma. According to this calculation, plasma concentrations would lie in the range of 2.1 to 2.8 µg/ml. Similar considerations make it highly unlikely that the amount of sLAM-1 found in serum or plasma is generated from the shedding of cell surface LAM-1 by blood leukocytes present during the preparation of the samples: the quantity of sLAM-1 actually found in serum is 10 to 25 fold higher than the quantity of LAM-1 that could maximally be shed from the cell-surface of leukocytes ($\sim 4\times10^6$/ml) present in the samples, assuming a density of 50–100,000 receptors/cell. Therefore, sLAM-1 must be generated by the ongoing shedding of cell surface LAM-1 from leukocytes in vivo.

sLAM-1 semipurified from plasma inhibited LAM-1-mediated lymphocyte binding to TNF-activated endothelium in a dose dependent manner with complete inhibition at ~8–15 µg/ml. At concentrations of sLAM-1 similar to those found in the plasma of normal blood donors, a small but significant inhibition of leukocyte endothelial binding was observed. Circulating sLAM-1 is likely to be functional in vivo since immunohistochemical staining of tissues with anti-LAM-1 mAb revealed sLAM-1 specifically bound to the luminal surface of endothelial cells, both on HEV-endothelium and at sites of inflammation.

Detection by Western Blot Analysis

In vitro, leukocytes and LAM-1 cDNA-transfected cells shed LAM-1 from the cell surface that can be detected in the culture supernatant fluid. To determine whether this process also occurs in vivo, the anti-LAM1-3 mAb, which identifies an epitope within the lectin domain, was used to immunoprecipitate reactive materials from normal human plasma. The precipitated materials were then analyzed by SDS-PAGE, transferred to nitrocellulose and the presence of a soluble form of LAM-1 was visualized by Western blot analysis using the anti-LAM1-14 mAb that binds to a LAM-1 epitope located within the SCR region. Two predominant isoforms of sLAM-1 were observed, a ~62,000 $M_r$ isoform and a 75–100,000 $M_r$ isoform. Analysis of the culture supernatant fluid from PMA-stimulated lymphocytes, neutrophils and K562 cells transfected with LAM-1 cDNA (K562-LAM) revealed different, cell-specific isoforms of sLAM-1. Neutrophils shed a 75–100,000 $M_r$ isoform of sLAM-1, that travelled as a broad band with an ill-defined upper border most likely due to heavy glycosylation (Ord et al., J. Biol. Chem. 265:7760–7767 (1990)). Lymphocytes generated a 62,000 $M_r$ isoform and K562-LAM cells shed a 71,000 $M_r$ isoform of sLAM-1. No specific proteins were isolated from the supernatant fluid of untransfected K562 cells using the above assays, and pre-clearing the plasma or supernatant fluid with the anti-LAM1-3 mAb eliminated subsequent Western blot results. Therefore, it is likely that the two predominant isoforms of sLAM-1 identified in plasma derived from both lymphocytes and neutrophils. Furthermore, sLAM-1 in serum contained the lectin, EGF and SCR domains as it was visualized in these experiments using mAb reactive with the lectin (anti-LAM1-3) and SCR (anti-LAM1-14) domains, but the $M_r$ of sLAM-1 is smaller than that for LAM-1 isolated from detergent solubilized cells as previously described (Lasky et al., Cell. 56:1045–1055 (1989); Spertini et al., Leukemia 5:300–308 (1991)).

Quantitation of sLAM-1 in Plasma and Serum by ELISA

The amount of sLAM-1 found in human plasma was quantitated with a sandwich ELISA using the anti-LAM1-5 mAb as a capture antibody and biotinylated anti-LAM1-3 mAb as a detecting antibody. This specific combination of mAb provided the highest level of sensitivity so that ~5 ng of sLAM-1 could be easily detected. The level of sLAM-1 determined by ELISA in the sera of a population of healthy normal blood donors was found to be 1.6±0.81.0 µg/ml, n=63. In some donors, sLAM-1 levels were simultaneously quantitated in plasma with similar results obtained (1.9±1.0 µg/ml, n=18). The possibility that sLAM-1 in plasma or serum might still be membrane bound was ruled out as the same levels of sLAM were found in serum and plasma before and after ultracentrifugation. sLAM-1 was stable in whole blood left to stand at 20° C. before separation of serum or plasma for up to at least 24 h. Storage of serum or plasma at 4° C. for up to three months in the presence of azide or repeated thawing and freezing (up to ten times) did not affect the ability to detect sLAM-1 in serum. It thus appears that sLAM-1 is present at relatively high levels in human plasma and serum.

Quantitation of sLAM-1 in Supernatants of Activated Leukocytes

Stimulation or the culturing of leukocytes has been associated with shedding of LAM-1 from the cell surface. In experiments carried out to determine if sLAM-1 accumulated, culture supernatant fluid obtained from an erythroleukemia cell line transfected with the pLAM-1 cDNA (K562-LAM) was found to contain detectable sLAM-1, in contrast to supernatant fluid obtained from untransfected cells cultured at the same density. Similarly, medium from freshly isolated neutrophils cultured at 37° C. for 60 min also contained detectable sLAM-1. Incubation of the neutrophils with stimuli that do not affect cell surface LAM-1 expression, granulocyte-colony stimulating factor, interleukin 1, monocyte-colony stimulating factor, interleukin 6, interferon γ, and interleukin 4, did not induce an increase in sLAM-1. However, stimulation with formylated methionine-leucine-phenylalanine, lipopolysaccharide, granulocyte/monocyte-colony stimulating factor, interleukin 8, and TNF induced LAM-1 shedding corresponding to their potency to stimulate cell surface expression. Culturing lymphocytes for 60 min at 37° C. caused some shedding of LAM-1, which was greatly enhanced by PMA-treatment. Quantitation of the amount of sLAM-1 found in the supernatant fluid following activation of neutrophils and lymphocytes ($1 \times 10^7$ cells/ml) varied between approximately 10 to 30 ng/ml. However, PMA-activation of lymphocytes for greater than 25 min, and neutrophils for greater than 10 min, resulted in the gradual degradation of sLAM-1. Degradation was not observed in the supernatant from K562-LAM cells, where sLAM was consistently found at concentrations of 22±6 ng/ml (1.7±0.5% of standard plasma; n=14). Elevated levels of sLAM-1 were also detected in the culture supernatant fluid of lymphocytes cultured with phytohemagglutinin, concanavalin A, and pokeweed mitogen for 3 to 6 d at 37° C. These mitogens are known to cause cell surface loss of LAM-1 (Tedder et al., J. Immunol. 144:532–540 (1990)). Thus, loss of LAM-1 from the cell surface directly correlates with an increase of sLAM-1 in the culture medium.

Inhibition of Lymphocyte Binding to Activated Endothelium by sLAM-1 sLAM-1 was semipurified from plasma by salt fractionation followed by affinity chromatography with the anti-LAM1-3 mAb, as described. The column eluate was concentrated and the level of sLAM-1 present was quantitated by ELISA and adjusted to ~15 µg/ml (6 to 10% of total eluate protein). sLAM-1, at different concentrations, in RPMI 1640/10% FCS was incubated (15 min, 4° C.) with cytokine-activated endothelial cells before examining lymphocyte attachment to endothelium through LAM-1. While sLAM-1 at physiological concentrations caused only partial inhibition of lymphocyte attachment (32.1±15.9%, n=10), it was found to inhibit most LAM-1-dependent lymphocyte binding at concentrations of 8 µg/ml (52 to 100%) and caused almost total inhibition of LAM-1 mediated binding at 12 to 15 µg/ml (93 to 100%). Lymphocyte binding mediated by LAM-1 was calculated as the difference between total binding at any given concentration of sLAM-1 and lymphocyte binding found in the presence of anti-LAM1-3 mAb which blocks all LAM-1 mediated adhesion (Spertini et al., J. Immunol. 147:2565–2573 (1991)). Importantly, sLAM-1 at 15 µg/ml caused no additional inhibition of lymphocyte binding beyond that obtained with anti-LAM-3 mAb alone. When the sLAM-1 samples were precleared with the anti-LAM1-15 mAb (which does not block LAM-1 function) before the assays, the preparation was not able to inhibit lymphocyte attachment demonstrating that sLAM-1 mediated the inhibition. Thus, it appears that sLAM-1 is capable of inhibiting LAM-1-specific lymphocyte adhesion to endothelium by binding to its putative endothelial ligand.

The inhibitory capacity of sLAM-1 at normal physiological concentrations (1.5 µg/ml) was further evaluated to determine if it could alter the interaction of lymphocytes with endothelium. Endothelium was activated with TNF (100 U/ml) for different periods of time to induce the LAM-1 ligand in a manner similar to what might happen during the initiation of an inflammatory response. During the course of induction of the LAM-1 ligand, sLAM-1 treatment of the endothelium caused a consistent, but small, inhibition of LAM-1-dependent lymphocyte attachment (30% at 2 h, 43% at 3 h, 41% at 4 h, 15% at 5 h and 22% at 6 h). Again, the combination of sLAM-1 with the anti-LAM1-3 mAb did not cause a greater inhibition than that observed with the mAb alone. Thus, during the development of an inflammatory response, it is likely that sLAM-1 will be able to alter the course of leukocyte attachment, although the influence appears to be small in this in vitro assay.

sLAM-1 in Serum Blocks anti-LAM-1 mAb Binding

The presence of circulating sLAM-1 was further verified by demonstrating that the reactivity of anti-LAM-1 mAb with LAM-1$^+$ cells could be inhibited by plasma. When lymphocytes were stained using anti-LAM-1 mAb in undiluted human plasma, no significant staining was obtained at concentrations of mAb that were saturating in RPMI/FCS. Next, lymphocytes ($1 \times 10^6/100$ µl) were incubated with various concentrations of LAM-1 directed mAb diluted (1:100) in autologous plasma or autologous plasma which had been precleared of sLAM-1 by immunoprecipitation. After completion of indirect immunofluorescence staining, antibody binding was assessed by flow cytometry. In most cases, the presence of plasma inhibited anti-LAM-1 mAb staining when the mAb were used at 2 to 5 µg/ml. Thus, ~13 to 33 pM IgG$_1$ (MW 150,000) bound to ~21 pM sLAM-1 (MW 75,000) based on the concentration of sLAM present in plasma (1.6 µg/ml) determined as outlined above. sLAM-dependent inhibition of mAb binding was seen in plasma for mAb which recognize the lectin-domain (anti-LAM1-3, -4, and -10) and the EGF-like domain (anti-LAM1-5, and -15). In contrast, binding of the anti-LAM1-1 mAb, which binds an epitope in the EGF-like domain, was not significantly inhibited by the presence of plasma.

The LAM1-1 Epitope Was Not Detected on sLAM-1 From Human Plasma

Since anti-LAM1-1 mAb binding to lymphocytes was not inhibited by plasma, the epitope identified by this mAb may not be present on sLAM-1. To examine this further, ELISA were performed in which different LAM-1-directed mAb were bound to an ELISA plate as capture antibodies with the anti-LAM1-3 mAb as the detecting antibody. Lectin domain-specific antibodies (anti-LAM1-6, -7, -10 and -11) and EGF-domain specific mAb (anti-LAM1-5 and -15) gave strong, easily detectable positive signals. Wells coated with the anti-LAM1-3 and -4 mAb, which cross-block the binding of the detecting antibody (anti-LAM1-3), served as internal controls for background reactivity. In contrast to all other mAb, anti-LAM1-1, gave a signal that was not significantly different from background, as defined by using BSA as the capture reagent. Thus, the epitope located within the EGF-region which is specifically recognized by the anti-LAM1-1 mAb appears to be lost from LAM-1 after shedding. As LAM-1 was easily recognized by all LAM-1-specific mAb in immunofluorescence staining of lymphocytes and all three extracellular domains are preserved on sLAM found in plasma, conformational changes in the sLAM-1 protein may lead to the loss of the EGF-domain related LAM1-1 epitope.

In order to determine whether the transmembrane or cytoplasmic regions of LAM-1 are necessary to uphold the complete tertiary structure of its extracellular domains, a second form of soluble LAM-1, a LAM-IgG fusion protein was generated and epitope-mapped by ELISA. The chimeric cDNA used to generate the fusion protein was constructed so that it contained essentially the whole extracellular region of LAM-1. Culture supernatant fluid of COS cells that were transiently transfected with the chimeric cDNA were tested for the production of LAM-IgG by ELISA. The anti-LAM1-5, -7, and -15 mAb, which detected sLAM-1 in plasma and in supernatant fluid from PMA-stimulated K562-LAM cells, also bound the LAM-IgG chimera at similar levels. In contrast, while the anti-LAM1-1 mAb failed to generate a significant signal with sLAM-1 from plasma and K562-LAM transfectants, it readily bound the LAM-IgG fusion protein. Thus, it is likely that sLAM-1 generated in vivo or in vitro loses a necessary conformational determinant that is required for anti-LAM1-1 mAb binding.

Expression of LAM-1 in Human Inflammatory Tissues

Presumably, sLAM-1 is generated in vivo as leukocytes become activated and/or transmigrate through endothelium. It has also been observed that leukocytes isolated from various tissues express little LAM-1 (Tedder et al., J. Immunol. 144:532–540 (1990)), suggesting that as the cells transmigrate the endothelium or localize in tissues, that they shed LAM-1. However, the presence of cell surface LAM-1 was not strictly restricted to leukocytes within blood vessels as revealed by immunohistochemical analysis: Extravascular leukocytes positive for LAM-1 were seen in all tissues examined, and these included, where present, lymphocytes, neutrophils and monocytes. The process of extravasation does not result in complete loss of cell-surface LAM-1 from all cells as lymphocytes which appeared to be traversing between endothelial cells remain LAM-1$^+$, and some transmigrating monocytes also appeared LAM-1$^+$. In general, monocyte/macrophages and granulocytes localized within tissues were largely LAM-1 negative, however, some extravasated neutrophils and macrophages were LAM-1$^+$. Most importantly, focal staining of venular endothelial cells was observed with anti-LAM-1 mAb in 2 of 4 hyperplastic lymph nodes, 2 of 3 sarcoid lymph nodes, on 1 of 4 rheumatoid synovia, in 1 of 3 specimens of inflamed skin, and 2 of 4 of appendicitis. This endothelial staining is consistent with the notion that sLAM-1 is capable of binding to its ligand on the apical surface of endothelium.

Experimental Procedures

Antibodies

LAM-1 directed mAb were the anti-LAM1-3, -4, -6, -7, -8, -10, -11, and -12 mAb directed against epitopes within the lectin domain, anti-LAM1-1, -5 and -15 reactive with epitopes within the EGF-like domain and anti-LAM1-14 which reacts with the SCR regions of LAM-1, all of the IgG$_1$ isotype (Spertini et al., J. Immunol. 147:942–949 (1991)). The anti-LAM-1 mAb were purified by salt fractionation followed by anion exchange chromatography, with the mAb concentration determined by light absorption. The anti-LAM1-3 mAb was bound to CNBr-activated Sepharose 4B (Pharmacia LKB Biotechnology, Piscataway, N.Y.) at 2.5 mg of mAb bound per ml of beads (anti-LAM-Sepharose) using the methods of the manufacturer.

Isolation of Blood Mononuclear Cells

Heparinized blood was obtained according to protocols approved by the Human Protection Committee of Dana-Farber Cancer Institute, Boston, Mass. Mononuclear cells were isolated by Ficoll Hypaque density gradient centrifugation. Cells were immediately suspended in RPMI 1640 (Gibco-BRL, Gaithersburg, Md.) containing 10% FCS and kept at 4° C. until use. In most instances, these cells will be referred to as lymphocytes since 85 to 95% of the cell population was lymphocytes as determined by morphology (Wright's stain) and flow cytometry analysis. Neutrophils were purified by centrifugation on a cushion of Mono-Poly Resolving Medium (Flow Laboratories, McLean, Va.) followed by lysis of the red cells with ice-cold hypotonic 0.2% (w/v) NaCl solution. Granulocytes were finally resuspended in HBSS containing 5% FCS (Sigma, St. Louis, Mo.). When sLAM was obtained for Western blot analysis, the mononuclear cells were first incubated in plastic dishes for 30 min in RPMI/10% FCS at 37° C. to remove adherent monocytes. Nonadherent cells retained surface LAM-1 and were predominantly lymphocytes (~99%).

Cell Cultures

Lymphocytes were cultured in 24 well plates (Costar Corp., Cambridge, Mass.) at $10^6$/ml in RPMI 1640 medium containing 10% FCS, 2% L-glutamine, penicillin, and streptomycin. The cells were cultured with PMA (100 ng/ml) for 60 min before the culture medium was harvested and tested for sLAM-1 by ELISA. Neutrophils were incubated in polypropylene tubes at $8 \times 10^6$ cells/ml for 60 min at 37° C. either in HBSS/5% FCS medium alone or containing granulocyte/monocyte-colony stimulating factor (25 ng/ml; a gift from Drs. Steven Clark and Gordon Wong, Genetics Institute, Cambridge, Mass.), monocyte-colony stimulating factor (100 ng/ml; Genetics Institute), tumor necrosis factor-a (TNF-α; 100 U/ml; Genzyme Corp., Cambridge, Mass.), lipopolysaccharide (1 µg/ml; Escherichia coli 011:B4; Sigma), formyl-methionyl-leucyl-phenylalanine ($10^{-8}$M; Sigma), interferon-γ (1000 U/ml; Genzyme Corp., Cambridge, Mass.), or interleukin-1β (10 U/ml; Genzyme Corp., Cambridge, Mass.). After culture, the supernatants were tested for the presence of sLAM-1 by ELISA. The human erythroleukemia cell line K562 was transfected with the pLAM-1 cDNA as previously described (Tedder et al., J. Immunol. 144:532–540 (1990)) and was be called K562-LAM throughout. These cells were cultured in RPMI 1640/10% FCS and were kept at cell numbers between 0.2 to $1 \times 10^6$ cells/ml. All cells were incubated at 37° C. in 5% $CO_2$ with 100% humidity.

Indirect Immunofluorescence Analysis

Indirect immunofluorescence analysis was carried out after washing the cells three times. Cells ($1 \times 10^6$ cells) were resuspended in 100 µl of media containing various concentrations of the indicated mAb, and incubated for 60 min at 4° C. After washing, the cells were treated with FITC-conjugated goat anti-mouse Ig antibodies (Southern Biotechnology Associates, Birmingham, Ala.) for 20 min at 4° C. The cells were washed, and fixed (1% paraformaldehyde in PBS), and single color fluorescence was determined on a flow cytometer (PROFILE™, Coulter Immunology, Hialeah, Fla.). Ten thousand cells were analyzed for each sample and the mean peak channel number for positively stained cells was determined using a linear scale.

In some experiments, cells were stained in the presence of human plasma. sLAM was precleared from an aliquot of the same plasma by immunoprecipitation with anti-LAM-Sepharose (1 ml of beads per 4 ml of plasma). The efficiency of the immunoprecipitations was tested by ELISA (<20 ng/ml). Lymphocytes ($1 \times 10^6$) were resuspended either in 100 µl of plasma or precleared plasma containing various concentrations of the purified mAb (added 1:100) as indicated. The cells were washed twice, stained and analyzed as above.

Endothelial-leukocyte Attachment Assay

Lymphocyte adhesion to cytokine-activated endothelium under non-static conditions was determined in a test system adapted from the Stamper/Woodruff assay for frozen tissue sections (Stamper Jr. et al., J. Exp. Med. 144:828–833 (1976)) exactly as described (Spertini et al., J. Immunol. 147:2565–2573 (1991)). Briefly, human umbilical vein endothelial cells (HUVEC) were isolated from cord veins, and grown in M199 medium supplemented with 10% FCS, endothelial cell growth factor (50 µg/ml, Biomedical Technologies, Inc., Stoughton, Mass.) and porcine intestinal heparin (50 mg/ml; Sigma) as described (Spertini et al., J. Immunol. 147:2565–2573 (1991)). Endothelial cells were grown to confluence on gelatin (0.1%) coated glass slides and stimulated with TNF-α (100 U/ml) at 37° C. for the times indicated. The monolayers were carefully washed, and incubated at 4° C. for 15 min with 75 µl of RPMI/10% FCS alone or containing semipurified sLAM-1. As a control, in some instances media containing semipurified sLAM-1 were precleared by immunoprecipitation with anti-LAM-Sepharose. Without further washing, $5 \times 10^6$ lymphocytes in 75 µl of the respective media were added. After 20 minutes of incubation at 4° C. with rotation at 64 rpm, the slides were rinsed, then fixed overnight in glutaraldehyde, (1% (v/v) in PBS; Polysciences, Warrington, Pa.), and stained with hematoxylin. The number of adherent leukocytes was determined by counting 6 microscopic fields (0.09 mm²/field) and the results were expressed as means ±SD.

Immunohistochemistry

Blocks of fresh human tissue were snap frozen. The specimens were peripheral lymph node (non-specific hyperplasia, 4 cases), sarcoid lymph node (3 cases), acute appendicitis (4 cases), rheumatoid synovium (4 cases), and inflamed skin (insect bite, delayed hypersensitivity reaction to tuberculin, and pityriasis lichenoides chronica; 1 case each). Immunohistochemistry was performed on cryostat sections using the anti-LAM1-3 mAb and an avidin-biotin-peroxidase method with diaminobenzidine (Rice et al., Am. J. Pathol. 138:385–393 (1991)). As a control, a murine IgG$_1$ (Coulter Immunology, Hialeah, Fla.) of irrelevant specificity was used at a concentration three times stronger than the test mAb. The control IgG did not produce detectable staining and thus all stated results refer to specific staining only obtained with the test mAb.

Production of the LAM-1 and IgG Chimera cDNA and Protein

The 1400-bp BanII fragment from a cDNA encoding the CH1 through CH3 domains of the human IgG$_1$ constant region was inserted at a BanII site introduced into pLAM-1 cDNA (Chin et al., J. Immunol. 125:1770–1774 (1980)) by oligonucleotide directed mutagenesis. The exchange of nucleotides in pLAM-1 cDNA from GAGGGT$^{1078}$ to GAGCCC created a BanII site corresponding to amino acid number 370 in the membrane proximal region of the mature protein. The antisense oligonucleotide used to generate the new restriction site, plus a sense oligonucleotide anchor from the plasmid 5' end of the pLAM-1 cDNA were used to amplify the 5' end of pLAM-1 cDNA. The PCR product was treated with T4 kinase, gel purified, subcloned into pSP65 (Promega Biotech, Madison, Wis.) and digested with BanII and KpnI. In parallel, the LAM-1 cDNA subcloned into pSP65 was digested with KpnI and PvuI, and a cDNA encoding human heavy chain IgG$_1$ was digested with BanII and PvuI. After gel purification, the DNA fragments thus obtained were mixed with the PCR product previously digested with KpnI and BanII and ligated together. The PCR product was sequenced, and the conservation of LAM-1 and IgG$_1$ restriction sites in the pLAM-IgG$_1$ DNA was confirmed by restriction mapping. The LAM-IgG$_1$ DNA was subcloned into the Ap$^r$M8 expression vector (provided by Dr. Lloyd Klickstein, Center for Blood Research, Boston, Mass.) and used to transiently transfect COS cells by the DEAE dextran method. The transfected COS cells were cultured in AIM-V serum-free media (Gibco-BRL0 and the supernatant fluid containing the chimeric LAM-1/IgG$_1$ fusion protein was harvested after 3 d.

Soluble LAM-1 Purification sLAM-1 was semipurified from plasma obtained from heparinized human blood. Plasma was salt-fractionated with Na$_2$SO$_4$ (18% w/v) before the sLAM-1 containing supernatant fraction was dialyzed against 0.02M Tris buffer (pH 8.0), 0.5M NaCl. The sLAM-1 preparation was further purified by affinity column chromatography using anti-LAM-Sepharose. sLAM-1 was eluted from the column with 0.1M Na acetate buffer (pH 3.5), 0.15M NaCl and the low pH of the eluate was immediately raised by the addition of 2.0M Tris buffer (pH 9.0). The pooled fractions of the eluate peak were ultrafiltrated and resuspended in PBS. The concentration of sLAM-1 was determined by ELISA and subsequently adjusted to approximately 15 µg/ml in PBS. At this sLAM-1 concentration, the total protein concentration of the samples varied between 130 to 220 µg/ml as determined by light absorption, and sLAM-1 represented ~6 to 10% of total protein. In general, this procedure gave a 2200 to 3700 fold enrichment for sLAM-1. For use in lymphocyte-endothelial adhesion assays, semipurified sLAM-1 was transferred into RPMI 1640/10% FCS by further ultrafiltration.

Western Blot Analysis sLAM-1 was semipurified from plasma as described above and further purified by immunoprecipitation using anti-LAM-Sepharose with repeated washing of the beads in alternating high salt (0.5M NaCl, 0.2% Na-deoxycholate) and low salt (0.125M NaCl, 0.05% Na-deoxycholate) RIPA buffer (100 mM Tris pH 8.0, 1% (v/v) Triton X-100, 10 mM EDTA, 10 mM EGTA, 10 mM NaF, 1 mg/ml BSA). Proteins were eluted from the beads with 0.1M acetate buffer (pH 3.5), 0.15M NaCl. Supernatant fluid from PMA-stimulated cells was also analyzed. Cells ($1 \times 10^7$/ml) including, neutrophils (10 ng/ml PMA in RPMI 1640 for 10 min at 37° C.), lymphocytes (10 ng/ml PMA in RPMI 1640 for 25 min at 37° C.) and K562-LAM transfectants (100 ng/ml PMA in PBS for 120 min at 37° C.) were induced to shed essentially all detectable cell surface LAM-1, before being pelleted by centrifugation (4° C., 400×g, 10 min). The supernatant fluid was saved and concentrated ten fold by ultrafiltration (Amicon Corp., Danvers, Mass.). Protein samples (100 μl) were applied to a 7.5% SDS-polyacrylamide gel, electrophoresed and blotted onto nitrocellulose. Western blot analysis was performed using the anti-LAM1-14 mAb (ascites, 1:2000) as the antigen detecting antibody. The blot was developed using alkaline phosphatase conjugated goat-anti-mouse $IgG_1$ antibody (Southern Biotechnology Associates) and NBT/BCIP as substrate (Promega, Madison, Wis.). In preliminary experiments, the anti-LAM1-14 mAb was the most sensitive of the twelve anti-LAM-1 mAb tested, of which anti-LAM1-3, -4, -8, -10, -14 and -15mAb were found to give positive staining.

Soluble LAM-1 ELISA

Wells of microtiter plates (96 well, flat bottom, E.I.A./R.I.A. plate, Costar, Cambridge, Mass.) were coated with anti-LAM-1 mAb (100 μg/ml) in 0.1M borate buffer, pH 8.4 at 4° C. for 18 h. Following two washes with Tris buffered saline (TBS; 20 mM Tris pH 7.5, 0.5M NaCl) the wells were blocked with 100 μl of 2% bovine serum albumin and 1% gelatin in TBS for 1 h at 37° C. The wells were washed three times with TBS containing 0.05% Tween 20 (TBST), and the test samples diluted into TBST (50 μl) were added to triplicate wells for 90 min at 20° C. Each assay included the titration of a previously quantified standard plasma sample that was used to generate a standard dilution curve. Dilution into fetal calf serum or pig serum had no significant effect on results. After being washed four times with TBST, the plates were incubated with 100 μl of biotinylated anti-LAM1-3 mAb (1 μg/ml) in TBST for 60 min at 20° C. After another four washes, 100 μl of avidin-horseradish peroxidase (0.1 μg/ml, Pierce, Rockford, Ill.) was added for 30 min at 20° C. After four more washes with TBST, the plates were finally developed using 100 μl of o-phenylenediamine (0.125% w/v, Sigma Chemical Co.) as a substrate in 0.1M citrate buffer, pH 4.5 in the presence of 0.015% $H_2O_2$. The OD of the reaction mixture was quantitated using an ELISA-reader (v-max, kinetic microplate reader, Molecular Devices, Menlo Park, Calif.). Results were obtained when the OD for the well containing the highest concentration of standard plasma was ~0.8 at 495 nM. Background OD values were obtained using wells coated with albumin only. The ELISA was made quantitative by using a standard plasma to generate a titration curve for each assay. The relative concentration of sLAM-1 in individual samples was calculated by comparing the mean OD obtained for triplicate wells to a semilog standard curve of titrated standard plasma using linear regression analysis. Sample concentrations were obtained by interpolation of their absorbance on the standard curve.

The amount of sLAM-1 present in the standard plasma was quantitated in two ways. First, K562-LAM-1 cells (~11 L of cultured cells, ~1.1×10$^{10}$ cells) were resuspended in PBS (1×10$^7$ cells/ml) and were stimulated with PMA (100 ng/ml) for 2 h at 37° C. The supernatant fluid was collected, concentrated by ultrafiltration and affinity purified by column chromatography using anti-LAM-Sepharose. The semipurified sample was electrophoresed on a 10% SDS-polyacrylamide gel that was subsequently stained by Coomassie-blue to reveal a prominent band of 71,000 $M_r$ and additional bands of ~180-, 57-, 47-, and 22,000 $M_r$. The destained gel was scanned using a Hewlett Packard Desk Scanner and the density of the 71,000 $M_r$ band was quantitated against a standard curve generated with BSA using the Enhance™ program (Microsystems, Des Moines, Iowa) on an Apple Macintosh IIcx computer. The concentration of sLAM-1 in the standard plasma was calculated to be ~1.3 μg/ml by comparing the signal from semipurified sLAM-1 to the LAM-ELISA titration curve of standard plasma with linear regression analysis. The detection limit of the LAM-ELISA was determined to be $\geq 5$ ng/ml. In a second set of experiments, COS cells were grown in serum free medium after transient transfection with the LAM-IgG chimera cDNA. Supernatant fluid was collected from the cells and run over a Protein-A Sepharose (Pharmacia LKB Biotechnology) affinity chromatography column, and the fusion protein was eluted from the column by high salt-low pH buffer. The purified fusion protein was quantitated after SDS-PAGE analysis by comparison of the stained protein band with a standard curve of BSA. From this analysis, it appeared that OD values for standard plasma would be equivalent to ~1.9 μg/ml of LAM-IgG fusion protein. Since the dimeric nature of the fusion protein might double the intensity of staining in our sandwich ELISA, the amount of sLAM-1 in the standard plasma may be half the value of ~1.9 μg/ml.

Test samples of human plasma, pig serum, and culture supernatant fluid from K562-LAM cells, LAM-IgG cDNA-transfected COS cells and mock transfected COS cells were examined in the ELISA for the presence of sLAM-1. Significant reactivity was only observed in the human plasma, and supernatant fluid from K562-LAM cells and LAM-IgG cDNA transfected cells. In ten assays, the LAM-ELISA had a linear correlation coefficient $\geq 0.97$ using a titration curve of standard plasma over a range of 5–1300 ng/ml. The interassay coefficient of variation for measuring sLAM-1 levels in plasma on three different days was 4.5%. There was no significant difference in sLAM-1 levels found between samples after freezing or after freezing–thawing up to ten times and no apparent decrease in ability to quantitate sLAM-1 amounts in whole blood left at room temperature for several hours. Therefore, sLAM-1 was quite stable in whole blood.

The amount of sLAM-1 found in a population of normal individuals was determined for serum (1.92±0.96 μg/ml, n=18). Plasma was also simultaneously isolated from the same individuals and quantitated in the LAM-ELISA, which gave average sLAM-1 levels of 1.91±0.98 μg/ml. sLAM-1 could also be detected in tissue culture supernatant fluid. Following lymphocyte activation with mitogens, increased levels of supernatant fluid sLAM-1 were detected by day 1 and levels increased over a 6-day culture period.

Use

Monoclonal antibodies that do not identify shed receptor LAM-1 yet identify the cell-surface receptor can be used as therapeutics for direct administration to patients. The use of antibodies of the invention will prevent many of the secondary side effects of antibody administration that may result from immune complex formation and cross-linking or binding of antibody to the soluble form of the receptor. Also, since the shed form of the receptor is a naturally occurring molecule present in high levels, it is possible to design recombinant protein products that are similar in structure to sLAM-1; i.e., a recombinant protein without a membrane spanning region and a cytoplasmic tail would mimic the natural serum protein. This characteristic would diminish the immunogenicity of such a recombinant to the species of origin and allow use of the receptor as a therapeutic product as well. Minor changes to the primary amino acid sequence of the receptor in the ligand binding region could be introduced to induce a higher binding constant or affinity for ligand. This modified, truncated recombinant protein could then be used in soluble form as a therapeutic with low immunogenicity yet a higher capacity to bind and block ligand binding of the cell-surface receptor protein.

Antibodies of the invention will also be useful as diagnostic agents. For example, the ability to identify leukocytes that express cell-surface LAM-1 is important for determining the migration potential of a given population of cells and the state of cellular differentiation and activation. Because of the high levels of sLAM-1, it will be difficult to use antibodies in the presence of biological fluids to identify the cell-surface molecule. However, antibodies like anti-LAM1-1 will be useful for identifying receptors present only on the cell-surface since they do not react with shed receptor in blood or biological fluid samples. For example, whole blood indirect immunofluorescence analysis will be facilitated and the in vivo imaging or analysis of receptor distribution will be possible with significantly lower amounts of antibody.

Also, monitoring of the levels of sLAM-1 could provide diagnostic or prognostic information relating to inflammatory disorders, leukocyte mobilization, malignancy or infection. For example, since levels of sLAM were easily and accurately quantitated in serum from normal individuals, serum levels of sLAM-1 were measured in patients with various states of systemic inflammation or infection. While patients with severe burns had sLAM-1 levels similar to those found in the normal population, serum from Kawasaki syndrome patients had sLAM levels generally less than those of normals. In contrast, patients suffering from sepsis or HIV-infection showed markedly elevated levels of sLAM-1 in serum that was significantly different ($p<0.005$) from that of a population of normal blood donors. sLAM-1 was also detected in cerebrospinal fluid, but the levels of sLAM-1 were generally only 0.6 to 6% of those found in normal serum. Thus, altered sLAM-1 levels, as an indication of leukocyte mobilization or activation, have diagnostic or prognostic value for inflammatory or infectious disorders.

The assays described herein demonstrate that detection of sLAM-1 levels in solution is readily achievable. Furthermore, quantitation of sLAM-1 levels in a very precise manner is also achievable, even when the sLAM-1 is contained within a biological fluid. Also revealed is that quantitation of sLAM-1 levels in biological fluids from patients may have diagnostic value.

One of ordinary skill, after reading the foregoing descriptions will be able to effect a variety of means for detecting not only sLAM-1, but also the parent protein LAM-1 or any fragment of LAM-1. Detailed descriptions of two binding assays have been provided, Western blot analysis and an antibody-based ELISA. However, other agents which bind selectively to LAM-1 may be used to capture or reveal the presence of LAM-1, or fragments thereof, such as carbohydrate moieties, including PPME, fucoidin or other LAM-1 ligands. Cell based capture mechanisms such as cytokine-activated endothelium or tissue sections that contain the LAM-1 ligand could also serve as binding agents.

In addition, the capture of LAM-1 or fragments thereof can be assessed by a variety of means obvious to those with skill in the art. For example, alterations in the structure, resonance or optical properties of the capture reagent or detecting reagent can be measured to reveal LAM-1 binding. The capture reagent may also be a polyclonal antiserum specific for LAM-1 or fragments thereof. Detection reagents can also be labeled using radioactive, immunoreactive, or enzymatically active agents or compounds to visualize binding. In addition, the capture reagent may not be specific for LAM-1 or fragments thereof, but LAM-1 specificity may be obtained through the use of LAM-1 specific detecting reagents, or the detecting reagent may be non-specific and the capture reagent specific.

Quantitation of the amount of LAM-1, or fragments thereof, present in a sample can also be achieved using a variety of means. For example, recombinant LAM-1 protein or fragments can be used as a standard as was demonstrated in the assay for naturally occurring sLAM-1 in serum or plasma. Also, LAM-1 or fragments thereof produced in tissue culture supernatant fluid of mammalian, bacterial or insect cells can be used. Even small peptide fragments which will bind to the capture reagent can be used to assess and quantitate LAM-1 binding in a competitive assay, or the displacement of small molecules from the capture reagent by LAM-1 can be used to quantitate the amount of LAM-1 present.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

Deposits

Hybridoma LAM1-1 was deposited on Jul. 28, 1991, with the American Type Culture Collection (ATCC) as ATCC No. HB10844.

Applicants' assignee, Dana-Farber Cancer Institute, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

What is claimed is:

1. A method for blocking LAM-1 dependent cellular adhesion in the presence of shed LAM-1, comprising the step of contacting a population of cells expressing said LAM-1 with an effective amount of a monoclonal antibody that is reactive with cell-surface bound LAM-1 but not reactive with shed LAM-1.

2. A method for inhibiting leukocyte migration into tissues, comprising the step of administering an amount of a monoclonal antibody that is reactive with cell-surface bound LAM-1 but not reactive with shed LAM-1, effective to block LAM-1 dependent cellular adhesion in the presence of shed LAM-1.

* * * * *